United States Patent [19]

Joustra et al.

[11] Patent Number: 4,626,355
[45] Date of Patent: Dec. 2, 1986

[54] METHOD OF DETERMINING ALCOHOL CONSUMPTION

[75] Inventors: Marius K. Joustra, Upsala; Claes G. Blanche, Sollentuna, both of Sweden

[73] Assignee: Pharmacia AB, Upsala, Sweden

[21] Appl. No.: 796,026

[22] PCT Filed: Feb. 6, 1985

[86] PCT No.: PCT/SE85/00061

§ 371 Date: Dec. 3, 1985

§ 102(e) Date: Dec. 3, 1985

[87] PCT Pub. No.: WO85/03578

PCT Pub. Date: Aug. 15, 1985

[30] Foreign Application Priority Data

Feb. 6, 1984 [SE] Sweden ................................. 8400587

[51] Int. Cl.$^4$ ............................................. B01H 15/08
[52] U.S. Cl. ..................................... 210/635; 210/656; 210/927; 436/161
[58] Field of Search ................. 210/635, 656, 927; 436/161

[56] References Cited

U.S. PATENT DOCUMENTS

4,507,390  3/1985  Horiuchi et al. .................... 436/161
4,579,661  4/1986  Gustafsson et al. ................. 210/927

OTHER PUBLICATIONS

Separation of Transferrin Types in Human Plasma by an Ion-Exchange High Performance Liquid Chromatography by Strahler et al. in Journal of Chromatography 266(1983), 281-291, Elsevier Scientific Pub. Amsterdam, Netherlands.
Quantification of a Transferrin Variant After Isoelectric Focusing in Agarose Gel Using Carbamylated Myoglobin as a Colored Marker by Petren et al. in Electrophoresis, vol. 5, pp. 26-29, Pub. 1984.
Quantative Analysis of Multiple Molecular Forms of Transferrin Using Isoelectric Focusing and Zone Immunoelectrophoresis Assay by Vesterberg et al. Journal of Immunological Methods, 46(1981), 53-62.
Chromafocusing: A Method for High Resolution Protein Purification by Richey et al. American Laboratory, pp. 100-110, Oct. 1981.
Evidence of Reduced Sialic Acid Content in Serum Transferrin in Male Alcoholics by Stibler et al. Alcoholic Clinical and Experimental Research, Karolinska Hospital, Stockholm, Sweden, pp. 545-549, Fall 1981.
Glycan Uniformity Within Molecular Variants of Transferrin With Distinct Affinity for Concanavalin A by Kerckaert et al. Biochemical and Biophysical Research Communications, vol. 105, No. 3, pp. 1023-1030, Apr. 1982, Academic Press, Lille Cedex, France.
Human Transferrin Asialotransferrin and the Intermediate Forms by Wong et al., McMasters University Health Science Center, Hamilton, Ontario, Canada, pp. 27-37, 1978.

*Primary Examiner*—John Adee
*Attorney, Agent, or Firm*—Fred Philpitt

[57] ABSTRACT

A method for determining the alcohol consumption of an individual by means of quantifying isotransferrin combinations in the individual's body fluids, these combinations being (A) isotransferrins having a pI higher than 5.6 or (B) isotransferrins having a pI higher than 5.8 or (C) isotransferrins having a pI higher than 6.0. The total concentration of any of said combinations (A), (B), (C) is a measure of the said individual's alcohol consumption during the last few weeks.

4 Claims, No Drawings

METHOD OF DETERMINING ALCOHOL CONSUMPTION

The invention is concerned with the determination of an individual person's alcohol consumption by means of quantifying isotransferrin in an isotransferrin-containing body fluid sample from the individual to be tested. This method utilizes the finding that isotransferrins of a certain pI can be correlated with an individual's alcohol comsumption; the particular names (different identities) of these isotransferrins are irrelevant and thus do not impose any restrictions on the practicability of the invention. On the basis of the correlation established between isotransferrins and alcohol consumption the invention can be a helpful tool in deciding about an adequate treatment program in each specific situation.

pH and pI values will vary with temperature and ion concentration. The pH and pI values set forth in the present specification and claims apply to a temperature of 23° C. and are measured in an aqueous solution of piperazine (20 mM total) buffered with formic acid to the pH or pH=pI in question. Thus the invention is not to be construed as being restricted to the particular values set forth: It comprises also any cases involving corresponding pH and pI values at other temperatures and ion concentrations.

Two major methods have been proposed earlier for determining the content of the aforesaid isotransferrins in a serum sample. One method is based on isoelectric focusing (IEF) (Stibler, H., Borg, S. and Allgulander C. Acta Med. Scand. 206 (1979), p. 275–81); it utilizes the fact that different isotransferrins migrating in a pH gradient under the action of an electric field will cover different distances depending on the pI values of the individual iso forms, these individually different pI values in turn being due to dissimilar contents of ionizable groups. In our particular case, the difference in pI values is believed to be due inter alia to different contents of sialic acid groups; it appears that isotransferrins have been discovered which have from 0 up to 5 sialic acid groups and have isoelectric points of 6.1, 5.9, 5.7, 5.5, 5.3 and 5.1, respectively. These isotransferrins will be referred to below as being, in that same order, asialotransferrin, monosialotransferrin, disialotransferrin, trisialotransferrin, tetrasialotransferrin and pentasialotransferrin, respectively. It is possible that each of these isotransferrins will be found later on to actually consist of a plurality of individual isotransferrins; however, for the sake of simplicity they are here treated as just one substance each.

The second one of the aforesaid two methods relies on utilizing the phenomenon that different isotransferrins have different types of terminal carbohydrate groups. Thus for instance, a desialo form characteristically lacks a sialyl group on at least one carbohydrate chain. One of the procedures employed with the framework of this second method (Cervén, E. et.al., Upsala J. Med. Sci. 86 xx (1981) p. 39–53) relies on the assumption that galactose is present as a terminal group of desialotransferrins. Cervén, E. et.al. therefore propose a procedure involving the use of a galactose-binding lectin for obtaining a biospecific affinity reaction between that lectin and the aforesaid assumed terminal galactose. At first a serum sample is contacted with an immunoadsorbent whereby transferrin—irrespective of its iso form—is caused to bind to said adsorbent. Then the transferrin-loaded adsorbent is separated, and the desialotransferrin attached thereto is to be detected with the aid of labeled galactose-binding lectin.

Both of these known methods involve heavy drawbacks. The IEF method is unpractical and takes too much time to be suitable for clinical routine work. In the course of our experiments for further developing a test according to Cervén, E. et.al. we have found that there is no correlation between the results obtained according to the lectin method and those obtained according to the IEF method. Obviously, therefore, these two methods do not measure the same items. It is not possible either, by means of the Cervén et.al. method, to bring out a significant difference between addict-type alcohol consumers and non-consumers of alcohol; the reason for this is probably that desialotransferrins lack not only sialic acid but also galactose—so the very concept of measuring desialotransferrin with the aid of a galactose-binding lectin is basically wrong. It is a known fact, moreover, that the affinity between lectin and sugar is weak. Also, the high background level encountered in this method may be due to sugar groups which are present on the transferrin adsorbent employed and tend to interfere with the lectin.

It will thus be appreciated that there is a great need for a simple and reliable method for determining alcohol consumption by means of an isotransferrin assay test. It is an object of the present invention to provide such a method which is suitable for clinical routine work and which measures specifically the concentration of such isotransferrins as can be correlated to the test alcohol person's consumption during the last few weeks preceding the test.

According to the invention, this is achieved by quantifying in a body fluid containing isotransferrin the total concentration of certain combinations of isotransferrins having pI values exceeding 5.6. These combinations are (A) isotransferrins of pI 5.7, 5.9 and 6.1; or (B) isotransferrins of pI 5.9 and 6.1; or (C) isotransferrin of pI 6.1. The total concentration of isotransferrins according to combination (A) or (B) or (C) is a measure of a person's alcohol consumption during the last few weeks before the sample has been taken.

According to one embodiment of the invention, a sample of the person's body fluid is contacted with an adsorbent capable of separating the isotransferrin inter se so as to give a fraction (I) containing at least one isotransferrin of pI greater than 5.6 and one or more fractions containing the bulk ($\geq 95\%$) of the remaining isotransferrins. After this separation the amount of fraction (I) transferrin is determined in a known per se manner. This amount is then a measure of the concentration of those isotransferrins in the sample which are characterized by a pI exceeding 5.6 and which have been carried over into fraction (I).

Fraction (I) thus contains isotransferrin according to any of the combinations (A), (B) or (C) above. Minor amounts of isotransferrin having a pI lower than 5.6 may be present in this fraction. The other fraction(s) contain(s) the isotransferrins that have not been transferred to fraction (I), and actually may contain some isotransferrins having a pI higher than 5.6. It is imperative at any rate that the aforesaid separation yielding the said fraction (I) be carried out in a reproducible manner for samples which are to be compared inter se.

Special embodiments are set forth in the appended claims.

The sample may be a body fluid sample, e.g. a serum sample, if desired diluted with a suitable buffer.

As regards the choice of adsorption methods, it is quite feasible to employ any one of them provided it is effective to bring about the aforesaid separation. Among chromatographic methods may be mentioned so-called batch methods and methods employing columns. For an operator having an average skill in the art it is an easy matter to find out, by some simple tests, whether or not a method is suitable in each individual case. In the present stage of the art the most advantageous procedure is ion exchange chromatography but it is also possible to employ other adsorption methods having a high selectivity for the isotransferrins contemplated here.

When proteins are subjected to ion exchange chromatography their separation is normally achieved with the aid of gradient or stepwise elution. In clinical routine work these procedures are thwarted by practical difficulties; but the separation can be carried out easily, in one step and in a short time, if an anion exchanger is used which has a high buffering capacity for a pH in a range between the isoelectric points of trisialotransferrin and asialotransferrin and which is set to a pH in that range. Before the chromatographic procedure is performed the sample should be diluted with a cation buffer having about the same pH as that to which the ion exchanger is set. Then the chromatographic procedure can be carried out in that the diluted sample is added, allowed to run through the ion exchanger, and then collected. If required more buffer solution may be added, but this is not necessary in the practice of the present invention. This type of chromatography is termed "isocratic"; it is performed at constant pH and constant ionic strength. Depending on the pH employed one of the desired combinations (A), (B) or (C) will be separated from the other known isotransferrins. In this procedure the pH and the high buffering capacity of the ion exchanger are utilized for obtaining the desired separation. Isotransferrins having a pI lower than the pH of the ion exchanger are adsorbed to the exchanger, whereas the isotransferrins having a higher pI are eluted.

In case the ion exchanger is a cation exchanger it should be adjusted to a pH within the same range as that set forth above for the anion exchanger, this adjustment being achieved with the aid of an anion buffer. The sample too is diluted with anion buffer. The chromatographic procedure will then result in adsorption of one of the desired combinations (A), (B) or (C) onto the ion exchanger, depending on the pH. The cation exchanger should have a high buffering capacity within the same pH range as the aforesaid anion exchanger.

In its most preferred embodiment (pH=5.65±0.02) the invention gives a high degree of correlation with the IEF method. In the 5.65±0.02 pH range the invention also provides better discriminative detection of high alcohol consumption than does the IEF method—probably because the method of the invention measures not only disialotransferrin but also monosialo- and asialotransferrins which too occur at increased levels in cases where alcohol consumption has been high.

Isocratic chromatography in accordance with the invention as compared to the IEF method has the great advantage of requiring much shorter times for its analyses. The time required to obtain each result in accordance with the IEF method will amount to about 5 days, as compared to the about 1.5 hrs required when the method of the present invention is employed.

The variables set forth below are important for carrying out the separation by means of isocratic ion exchange chromatography with an anion exchanger.

The most suitable pH for the separation is determined by the isoelectric points of the isotransferrins to be separated. The isotransferrins of clinical interest are disialo-, monosialo- and asialotransferrin of pI 5.7, 5.9 and 6.1 respectively. The other isotransferrins, which have no clinical relevance in the context of excessive alcohol consumption, are pentasialo-, tetrasialo- and trisialotransferrin of pI 5.1, 5.3 and 5.5 respectively. To attain a good reproducibility of the separation procedure it is suitable to choose a pH for the ion exchanger within any one of the following three ranges: (A) pH 5.5 to 5.7, preferably 5.65±0.02; (B) pH 5.7 to 5.9, preferably 5.80±0.02; (C) pH 5.9 to 6.1, preferably 6.00±0.02. In case of alternative (A) the pH value chosen is intermediate between the pI values of tri- and disialotransferrins respectively; consequently the disialo, monosialo and asialo forms will pass through the column and can be collected. In case of alternative (B) monosialotransferrin and asialotransferrin will pass through the ion exchanger, and in case of alternative (C) asialotransferrin will pass through. In providing these alternatives (A), (B) and (C) the invention in its most preferred embodiments makes it possible to adequately take into account also the potential presence of monosialo- and asialotransferrins.

In order for an anion exchanger to perform a fully satisfactory separation it should have a very high and uniform buffering capacity in the separation range contemplated. This capacity should be higher than 3 milliequivalents per 100 ml of ion exchanger and pH unit within the pH range of from 5 to 6.5.

An example of a suitable ion exchanger is the polyion exchanger PBE 94 (Pharmacia Fine Chemicals AB, Sweden). This exchanger is based on a crosslinked agarose having a large number of charged groups attached to its monosaccharide units via ether bonds, these charged groups being selected specifically for giving a high and uniform buffering capacity over the pH range contemplated.

Before the sample solution is added the ion exchanger should be conditioned to a pH in confirmity with one of the aforesaid pH ranges (A), (B) or (C).

In practicing the method an adsorbent volume of 50 to 150 $\mu$l is suitable. The volume of the diluted sample may be as large as 5 to 10 times the adsorbent volume without affecting the pH of the ion exchanger or the separation result.

The separation may be performed at temperatures within a wide range—for example at 15°–35° C., especially 21°–25° C.

The buffer should be of the cation type in order to prevent adsorption of buffering substances to the anion exchanger. The term "cation type buffer" refers to a buffer whose buffering component is potentially cationic at the pH comtemplated. The pKa value of the buffer substance should suitably be chosen so as to fall within the pH range (pH 5–6.5) of the separation procedure, preferably within one of the aforesaid pH ranges (A), (B) or (C). The buffering capacity of the buffer should be high but is not a critical factor in the method of this invention because the adequate buffering is provided for by the ion exchanger. The temperature dependence of the buffer should be similar to that of the pI of the isotransferrins.

Ionic strength should be low so that it will not affect the actual course of the separation which, for the reasons explained above, is pH-dependent. A suitable concentration of buffer substance is one within the range of from 20 to 30 mM, the concentration of the oppsitely charged ion then being 25 to 50 mM.

Among the buffering systems studied up to now, the best ones are found to be the following: 20 mM piperazine hexahydrate—formic acid, or 30 mM bis-(2-hydroxyethyl)-piperazine—formic acid, adjusted with the aid of formic acid to a desired pH the value of which depends on the separation alternative desired. The piperazinium ion pKa is 5.56 at 23.5° C. (Handbook of Chemistry and Physics).

The volumetric amount of the sample is not a critical factor for the separation procedure. If the amount if ion exchanger is (say) 100 μl it will be suitable to use sample volumes of 10–50 μl serum diluted with buffer to a final volume of 200–1000 μl which is poured onto the column.

For 100 μl of adsorbent, the sample volume currently believed to be optimum amounts to 20 μl of serum diluted to a 500 μl final volume with a suitable buffer.

The statement above that the determination procedure following after the separation is carried out "in a known per se manner" implies that in this stage recourse may be had to any method that is sufficiently sensitive and specific. Many of the current and preferred methods rely on an antigen-antibody reaction for this determination—that is, they belong to the large group of so-called immunological determination methods. Numerous techniques within this immunological field are known to the artisan. All of these methods are potentially applicable to the invention even though some of them are more suitable than others, in view of e.g. such factors as specificity, sensitivity or selectivity inherent in a particular technique. As an example may be mentioned procedures utilizing at least one labeled reactant. Determination methods of this type are described elaborately in the literature, see for example the specification and claims of GB-A-1552607 and GB-A-1548741. Alternative determination methods are turbidimetric determination (light scattering immunoassays), (Price, C. P. et al. Am. Clin. Biochem. 20 (1983), p. 1–14) and "Sol Particle Immunoassay"—e.g. agglutination of antibody-coated gold particles by reaction with immunochemical bivalent or multivalent antigens (transferrin) (Leuvering, J. H. et al. J. Imm. Meth. 62 (1983) p. 163–174).

In certain cases determination methods of generally the aforesaid type may utilize biospecific affinity relationships other than antigen-antibody affinity. These will then work in an equivalent manner. Examples of pairs of biochemical species having such other biospecific affinities of some sorts are: Protein A-IgG; carbohydrate-lectin; Clq-immunocomplex; RF factor-immunocomplex; biotin-avidin; etc.

The invention will be further illustrated below by way of a number of non-limitative working examples one of which comprises a comparative study in relation to previously known methods.

EXAMPLE 1

Determination of isotransferrin pI

Transferrin was purified from (i) a serum pool from addicted alcohol consumers and (ii) a serum pool from blood donors. The transferrin was then separated into its individual isotransferrins (pentasialo-, tetrasialo-, trisialo-, disialo-, monosialo- and asialotransferrins) in a FPLC system (Pharmacia Fine Chemicals AB, Sweden).

The ion exchanger was an anion exchanger column (Mono-Q, Pharmacia Fine Chemicals AB, Sweden), and the elution system employed was a linear pH gradient obtained with the aid of successive mixes of two solutions, viz., solution A=20 mM piperazine hexahydrate adjusted to pH 6.8 with 5M formic, and solution B=20 mM piperazine hexahydrate adjusted to pH 4.8 with 5M formic acid. These two solutions conjointly provide for a linear pH gradient ranging from pH 6.8 to pH 4.8. The system is tempered to 23° C.

The transferrin sample is applied to the column having an initial pH of 6.8. At this pH all the isotransferrins have a negative charge and therefore attach to the ion exchanger. When the pH is lowered within the range of the gradient the charge of each isotransferrin will progressively change from negative to less negative and finally to zero. The exact pH conditions under which an isofransferrin will proceed to zero charge will vary from isotransferrin to isotransferrin. When its charge is zero the transferrin will be released from the ion exchanger; it is then eluted through and from the column by being entrained in the eluent. The "isoelectric point" is this very point at which the charge of the isotransferrin is zero. A spectrophotometer is used to indicate when the isotransferrin leaves the column, and in this stage fractions are collected corresponding to the spectrophotometer recordings for each of the isotransferrins. In these fractions, which contain the different zero charge isotransferrins, the pH is measured; in each case this measured pH corresponds directly to the isoelectric point (pI) of the isotransferrin in that fraction.

It will be seen that these experiments have been carried out with the same buffer system (20 mM piperazine hexahydrate-formic acid) and at the same temperature (23° C.) as in Example 2. The pI values obtained therefore can be used for prescribing the pH for the separation of the isotransferrins to be searched for.

The pI values of the individual isotransferrins as thus determined according to the present Example are the following:

|  | Blood donors | Addicted alcohol consumers |
|---|---|---|
| pentasialo | 5.1 | 5.1 |
| tetrasialo | 5.3 | 5.3 |
| trisialo | 5.5 | 5.5 |
| disialo | 5.7 | 5.7 |
| monosialo | fnd | 5.9 |
| asialo | fnd | 6.1 |

"fnd" means "fraction not detectible" because its concentration is too low to be detected.

EXAMPLE 2

Isocratic chromatography for separation and determination of the individual isotransferrins Packing of gel in columns 100 ml of polyion exchanger PBE 94 obtained by allowing a particle suspension to settle (Pharmacia Fine Chemicals AB, Sweden) were mixed with 900 ml of 24% ethanol (v/v in water) to form a slurry. From this slurry 1 ml was pipetted into a microcolumn. The gel was allowed to settle in the column whereupon most of the ethanol was decanted, so that then only the gel sediment was left in the column.

The gel was then conditioned to the desired pH by means of 1.5 ml of piperazine hexahydrate-formic acid buffer, 0.020M in piperazine adjusted with 5M formic acid to pH 5.65 and containing 0.1% Tween® 20 (polyoxyethylene sorbitan laurate, Atlas Chemical Ind. Inc.) at 23° C. When all of the buffer solution had passed through the column (about 45 min.) the gel was ready for use.

Isotransferrin separation

20 µl of a serum sample were diluted with 480 µl of the above piperazine buffer and added to the conditioned microcolumn. The eluate (500 µl) was collected in a test tube. When after about 15 minutes the column had ceased to drip it was discarded and the eluate was recovered.

Fixing antibody to solid phase

Agarose (particle size 1-5 µm) was CNBr activated in a manner analogous to that described in U.S. Pat. No. 3,645,852.

To 10 g of activated particles were added 5 ml of sheep-antirabbit antibodies and 45 ml of 0.1M $NaHCO_3$, pH 8. This mixture was incubated overnight at +4° C. Thereafter the gel was centrifuged at 2000 g for 10 minutes whereupon it was washed at first with Tris buffer (0.05M tris-(hydroxymethyl)-aminomethane adjusted to pH 8.1 with hydrochloric acid) containing 1M NaCl and then with acetate buffer (0.1M, adjusted to pH 4.0 with hydrochloric acid) containing 1M NaCl. Residual active groups on the gel were blocked by means of ethanolamine (1.0M, adjusted to pH 9.0 with hydrochloric acid) for 60 minutes at room temperature. Finally the gel was twice subjected to washes with Tris buffer and acetate buffer in alternating succession, whereupon it was diluted to a concentration of 10 mg/ml with phosphate buffer (0.05M, pH 7.4) containing 0.15M NaCl, 0.02% $NaN_3$ and 0.1% Tween® 20.

Isotransferrin determination

To the eluate or to a test tube containing a known amount of transferrin were pipetted, in the order as stated, 100 µl of $^{125}I$ transferrin (22 ng/ml) (produced by iodination of transferrin as described by Greenwood, Hunter in Biochem. J. 89 (1963), p. 114), 100 µl of rabbit anti-transferrin antibody solution diluted 1:500 (DAKOpatts, Denmark), 2 ml of antibody (10 mg/ml) fixed to solid phase (as described above).

Next the tube was incubated for 60 minutes at room temperature without shaking, and this was followed by centrifugation at 2000 g for 10 minutes. The supernatant was then discarded by decanting (composition as set forth above).

Residual activity in the tube was measured by means of a gamma counter during 1 minute. This was done on a number of serum samples obtained from non-consumers of alcohol and from addicted alcohol consumers. The values measured are listed in Table 1.

With the aid of the corresponding piperazine-formic acid buffer set to pH 5.80±0.02 the corresponding values of total mono- and asialotransferrins were measured. These values too are listed in Table 1.

Any contents of the above-discussed isotransferrins in any unknown samples may be determined in this manner, in that the measured values are compared with corresponding values obtained from standard samples containing known amounts of transferrins.

EXAMPLE 3

Comparison of (i) the method of the present invention, (ii) the IEF method and (iii) the lectin method The lectin method (Cervén, E. et al., Upsala J. Med. Sci. 86 (1981) p. 39.52) and the IEF method (Stibler, H., Borg, S. and Allgulander, C., Acta Med. Scand. 206 (1979) p. 275-81) were carried out on serum samples some of which came from the same persons and were taken on the same occasion as those in Example 1. The results together with those obtained in accordance with Example 1 are listed in Table 1.

From this Table it will be seen (1) that there is an unmistakably clear correlation between the IEF method and the present novel method (correlation coefficient r=0.7);

(2) that there is no such clear correlation between the lectin method on one hand and either the present novel method or the IEF method on the other hand;

(3) that the present novel method and the IEF method give a degree of discrimination between non-consumers of alcohol and addicted consumers which has to be regarded as significant whereas the lectin method does not give a significant degree of discrimination; and (4) that the discrimination obtained with the present novel method is better than that obtained with the IEF method.

According to results obtained during the priority year the correlation with alcohol comsumption can be improved if the transferrin in sample is saturated with ferric ions. This is accomplished by adding a few drops of concentrated ferric citrate solution to the serum sample or diluting a definite volume of serum in less concentrated ferric citrate solution.

TABLE 1

| | Percentage of disialotransferrin acc to IEF method | Bound radioactive lectin acc to lectin method (cpm) | Amount of di-, mono-, asialotransferrin acc to present method (= invention) (µg/ml serum) pH | |
|---|---|---|---|---|
| | | | 5.65[1] | 5.80[2] |
| Non-consumers of alcohol | 2 | ND | 47 | 11 |
| | 3 | ND | 73 | 14 |
| | 5 | ND | 51 | 17 |
| | 5 | 17 018 | 64 | 18 |
| | 7 | 17 218 | 67 | ND |
| Addicted alcohol consumers | 3 | 18 739 | 93 | ND |
| | 6 | ND | 134 | ND |
| | 6 | ND | 115 | ND |
| | 7 | ND | 194 | ND |
| | 8 | ND | 129 | ND |
| | 8 | ND | 137 | ND |
| | 9 | ND | 134 | ND |
| | 9 | ND | 197 | ND |
| | 10 | 18 267 | 161 | 77 |
| | 10 | 17 129 | 152 | 65 |
| | 13 | 16 222 | 260 | 96 |
| | 13 | ND | 163 | 94 |
| | 16 | 17 304 | ND | ND |
| | ND | 16 931 | 162 | ND |

ND = not done
[1] pH 5.65 is used for determining disialo-, monosialo- and asialotransferrins
[2] pH 5.80 is used for determining monosialo- and asialotransferrins

We claim:

1. In a method for determining the alcohol consumption of an individual by means of quantifying isotransferrin in a body fluid sample obtained from said individual and in subjecting the said body fluid sample to an isocratic chromatography procedure on an ion-exchanger conditioned to a pH within a range having a lower pH limit no lower than the pH equal to the pI of an isotransferrin of pI 5.5 and having an upper pH limit no higher than the pH equal to the pI of an isotransferrin of pI 6.1 so that the total amount of the isotransferrins is separated into (i) a fraction (I) which contains at least one isotransferrin having a pI higher than 5.6 and (ii) one or more fractions which contain(s) the bulk of the remaining isotransferrins having pI values lower than those of the isotransferrins which have a pI higher than 5.6 and have been transferred to fraction (I), whereupon the total amount of isotransferrin(s) in fraction (I) (=the total amount of transferrin in fraction (I)) is determined in a manner known per se and is correlated in a manner known per se with the total concentration of those isotransferrins in said sample which have a pI higher than 5.6 and have been transferred to fraction (I).

2. A method according to claim 1 in which said isocratic chromatography procedure is carried out at a pH within a range having as its lower pH limit the pH equal to the pI of an isotransferrin of pI 5.5 and having as its upper pH limit the pH equal to the pI of an isotransferrin of pI 5.7.

3. A method according to claim 1 in which said isocratic chromatography procedure is carried out at a pH within a range having as its lower pH limit the pH equal to the pI of an isotransferrin of pI 5.7 and having as its upper pH limit the pH equal to the pI of an isotransferrin of pI 5.9.

4. A method according to claim 1 in which said isocratic chromatography procedure is carried out at a pH within a range having as its lower pH limit the pH equal to the pI of an isotransferrin of pI 5.9 and having as its upper pH limit the pH equal to the pI of an isotransferrin of pI 6.1.

* * * * *